March 23, 1976 A. W. FISCHER Plant Pat. 3,849
AFRICAN VIOLET PLANT
NAMED KARLA
Filed March 27, 1975
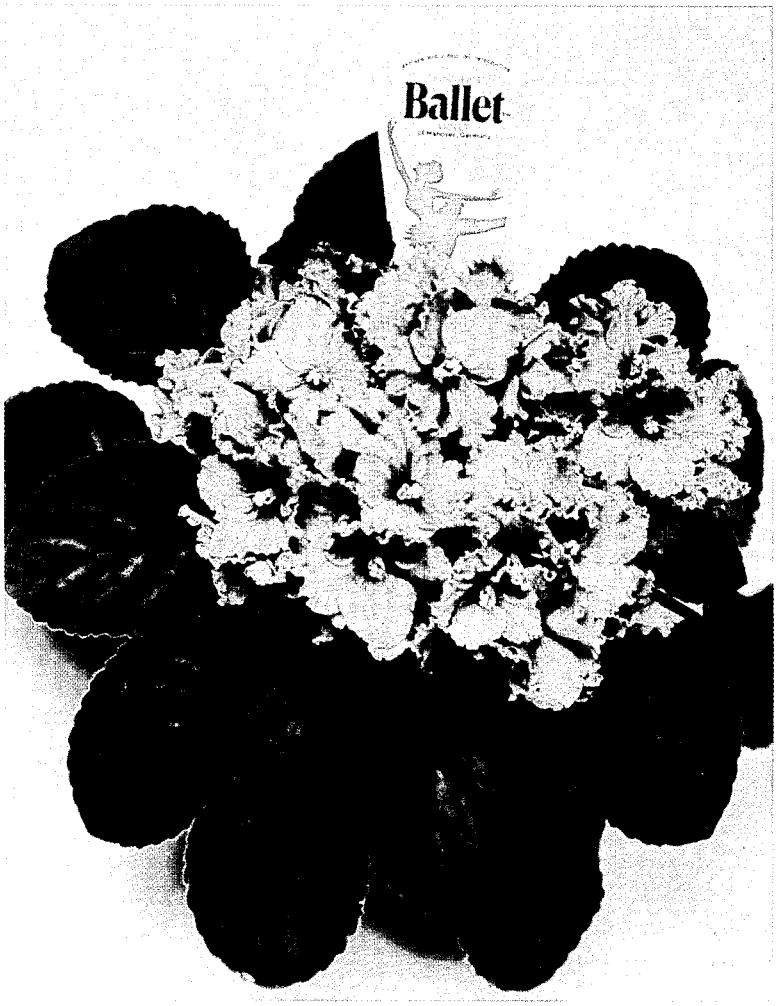

United States Patent

Plant Pat. 3,849
Patented Mar. 23, 1976

3,849

AFRICAN VIOLET PLANT NAMED KARLA

Arnold W. Fischer, Isernhagen, Germany, assignor to Geo. J. Ball, Inc., West Chicago, Ill.

Filed Mar. 27, 1975, Ser. No. 562,941
Int. Cl. A01h
U.S. Cl. Plt.—69 1 Claim

ABSTRACT OF THE DISCLOSURE

A new variety of African violet plant for potted plant culture characterized by a profuse production of medium sized flowers of unique color which are carried on strong, upright peduncles and fully cover the center of the plant above an abundant display of strong, dark green, horizontally spreading foliage. This new plant is further distinguished by its vigorous growing habit, compact form, and long lasting flowering cycle.

BACKGROUND OF THE NEW PLANT

This new African violet plant originated as a seedling from a cross of two unnamed and unpatented varieties selected by me from my stock of violet plants maintained at Isernhagen, Germany, for the breeding of improved African violet plants for the commercial market. This crossing was made by me with the object of developing a plant having improved growing and flowering performance, a novelty flower color, and a long lasting flowering cycle and the instant plant was selected for propagation and trial because it appeared to me to have characteristics of the kind that I was seeking to develop.

Propagation of this new plant, carried on under my direction at Isernhagen, Germany, by means of leaf cuttings since 1972, has demonstrated that the distinguishing characteristics which led to my selection of this plant appear to be firmly fixed and to hold true from generation to generation and propagation on a commercial scale, by leaf cuttings and shoot divisions, is now being done at West Chicago, Ill., U.S.A.

DESCRIPTION OF THE DRAWING

My new variety of African violet plant is illustrated by the accompanying photographic drawing which shows, in full color, the characteristics of its flowers and plant form, the color rendition being as nearly true as it is reasonably possible to obtain by conventional professional photographic procedures.

DESCRIPTION OF THE NEW PLANT

The following is a detailed description of my new variety of African violet plant with color specification according to the Horticultural Colour Chart (HCC) developed by Robert S. Wilson and published by the Royal Horticultural Society at London, England, in collaboration with the British Colour Council.

THE PLANT

Origin: Seedling.
Parentage:
- *Seed parent.*—68–14 (unpatented).
- *Pollen parent.*—069–13 (unpatented). These plants are unnamed varieties identified in my records by the stated numbers and maintained in my African violet breeding stock.

Classification:
- *Botanic.*—Saintpaulia Ionantha.
- *Commercial.*—African violet.

Form: Compact potted plant (rosette arrangement).
Height: 3 to 4 inches from base to top of flowers.
Growth: Vigorous, uniform and condensed with fairly strong petioles which tend to spread horizontally.
Foliage: Quantity—abundant.
- *Size of leaf.*—About 3 inches long and 2½ inches wide.
- *Shape of leaf.*—Ovate with crenate margins.
- *Texture.*—Very velvety.
- *Color.*—Upper side—Ivy Green 0001060/3. Under side—Maroon 1030/3 with Sage Green 00861 along margin.
- *Petioles.*—Length—3 to 4 inches.
- *Ribs and veins.*—Pronounced.

THE BUD

Form: Globular at first, becoming urn-shaped as it opens.
Size: About ¼ inch when about to unfurl.
Opening rate: Very slowly—about 5 weeks from visible but to opening flower.
Color: In general, when petals begin to unfurl, Rhodamine Purple 29/3, turning to Peony Purple 729.
Sepals: Hooded over the bud for only a short period of time.
- *Color.*—Inside—Fern Green 0862/3. Outside—Garnet Brown 00918.

Pedicel: ½ to ¾ inch long. Hairy and slender.
- *Color.*—Generally Maroon 1030.

THE FLOWER

Blooming habit: Profuse and recurrent.
Size of flower: Medium—1¾ inch x 1¾ inch,
Shape of flower: Cup-shaped when bloom first opens, changing to become flat as flower ages.
Borne: The influorescence of this plant is a cyme.
Petalage: Number of petals—5.
- *Arrangement.*—Sympetalous.
- *Form.*—Rotate with bilateral symmetry and frilled edges.
- *Texture.*—Soft.
- *Appearance.*—Glittery on upper surface, satiny on under side.
- *Color.*—Outer petals—Rhodamine Purple 29/2. Base of inside petals and veins in all petals—Peony Purple 729/2. Reverse side—Fuchsia Purple 28/3.
- *Petaloids.*—None.

Peduncle: 2 to 2½ inches long, sturdy and upright.
- *Strength.*—Sturdy and upright.
- *Color.*—Garnet Brown 00918/3.

Discoloration after full bloom: Center becomes Peony Purple 729 and the mid-area to edge becomes Fuchsia Purple 28/2.
Effect of weather: Extreme hot weather affects flowering.
Persistence: Flowers hang on and dry.
Fragrance: None.
Lasting quality: 10 to 14 days for the fully opened flower.

REPRODUCTIVE ORGANS

Stamens:
- *Anthers.*—Two in number, each having two anther cells in basifixed arrangement, about ⅛ inch in length, and Lemon Yellow 4 in color.
- *Filaments.*—Approximately 3/16 inch long.
- *Pollen.*—Color—Aureolin 3.

Pistils: One only.

*Stigma.*—Color—Rhodamine Purple 29/2.

*Style.*—Approximately 3/16 inch long.

Ovaries: Typical of African violets.

The distinctive features of this new African violet plant reside in the unique color characteristic of its flowers and its profuse production of flowers borne on upright peduncles so as to fully cover the center of the plant; its long lasting flowering cycle and vigorous growth habit; and its attractive dark green, laterally spreading foliage.

I claim:

1. A new variety of African violet plant, substantially as herein shown and described, characterized by its profuse production of uniquely colored blossoms which cluster to fully cover the center of the plant, its abundant dark green, horizontally spreading foliage, and vigorous growth habit and long lasting flowering cycle.

No references cited.

ROBERT E. BAGWILL, Primary Examiner